United States Patent [19]
Bailey et al.

[11] Patent Number: 4,888,352
[45] Date of Patent: Dec. 19, 1989

[54] 3,4, OR 5-ARYL-1H-PYRAZOLE-1-ALKANAMIDES AS ANTIARRHYTHMIC AGENTS, COMPOSITIONS AND USE

[75] Inventors: Denis M. Bailey, East Greenbush; Virendra Kumar, Colonie, both of N.Y.

[73] Assignee: Sterling Drug Inc., New York, N.Y.

[21] Appl. No.: 327,212

[22] Filed: Mar. 22, 1989

[51] Int. Cl.$^4$ .................. A61K 31/415; C07D 231/12
[52] U.S. Cl. ..................................... 514/406; 514/212; 514/326; 540/603; 546/211; 548/374; 548/378
[58] Field of Search ....................... 540/603; 546/211; 548/374, 378; 514/212, 326, 406

[56] References Cited
U.S. PATENT DOCUMENTS
4,072,498 2/1978 Moon et al. ............................. 71/92

FOREIGN PATENT DOCUMENTS
299407 1/1989 .

Primary Examiner—Robert W. Ramsuer
Attorney, Agent, or Firm—Philip E. Hansen

[57] ABSTRACT

N-[(disubstituted amino)alkyl]-3,4 or 5-aryl-1H-pyrazole-1-acetamides, useful for treating cardiac arrhythmias in mammals, are prepared by reacting a lower-alkyl ester of pyrazole-1-acetic acid with an appropriate diamine.

11 Claims, No Drawings

3,4, OR 5-ARYL-1H-PYRAZOLE-1-ALKANAMIDES AS ANTIARRHYTHMIC AGENTS, COMPOSITIONS AND USE

BACKGROUND OF THE INVENTION

Field of the Invention

The present invention relates to novel N-[(alkylamino) alkyl]-3,4,or 5-aryl 1H-pyrazole-1-acetamides, processes for the synthesis of said pyrazole-1-acetamides, and methods for treating cardiac arrhythmia in mammals utilizing said pyrazole-1-acetamides.

Information Disclosure Statement

U.S. Pat. No. 4,695,566 to Heinemann et al. discloses as anti-arrythmic agents 1H-pyrazol-3-yl(and 1H-pyrazol-5-yl) oxyacetamides of general formula

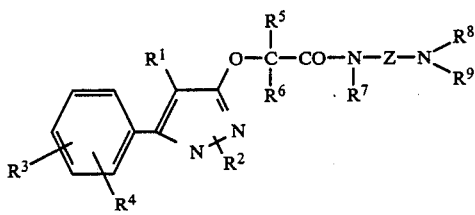

Specifically disclosed are (1) N-[2-(diethylamino)ethyl]-2[(5-phenyl-1H-pyrazol-3-yl)oxy]acetamide, example 5, and (2) N-[3(diethylamino)propyl]-2-[(5-phenyl-1H-pyrazol-3-yl)oxy]acetamide, example 24.

U.S. Pat. No. 4,182,895 to Bailey discloses as an intermediate in the synthesis of 1-amino-lower-alkyl-3,4-diphenyl-1H-pyrazoles "β-[1(3,4-diphenyl-1H-pyrazolyl)]-N,N-dimethylpropionamide" at column 8, line 63 to 64.

Bondavalli et al. [Farmaco, Ed. Sci 43, 725–743 (1988)]disclose Nalkyl carbamates of 1-(2-hydroxyethyl)-3,5-diphenyl-1H-pyrazole as antihypertensive, antiarrhythmic, analgesic, antiinflammatory and hypoglycemic agents. Specifically disclosed are the ethyl, isopropyl, phenyl and 1-naphthyl carbamates.

German published application 3,620,825 [*Chemical Abstracts* 108: 112467 (1987)]appears to disclose 3-phenyl-1H-pyrazole-1-acetamide as an intermediate in the synthesis of optical brighteners.

U.S. Pat. No. 4,072,498 to Moon and Kornis discloses a series of α-methyl-3-phenyl and 5-phenyl-1H-pyrazole-1-acetamides and a 3-phenyl-1H-pyrazole-1-propanamide as herbicides. Specifically disclosed are the o-chloro, m-chloro, and m-nitro as well as the unsubstituted 3-and 5-phenyl N,N,α-trimethyl-1H-pyrazole-1-acetamides (examples 15,21,16,25, and 2 respectively.) Example 124 discloses N,N-dimethyl3-phenylpyrazole-1-propionamide. Example 142 discloses N,N,α-trimethyl3-(o-fluorophenyl)pyrazole-1-acetamide as well as the corresponding o-bromo and o-ethyl analogs.

Ezrin et al. [*FASEB Journal* 2, A1557(1988)]describes the antiarrhythmic activity of N-[3-(diethylamino)propyl-4,5-diphenyl1H-pyrazole-1-acetamide fumarate.

European patent application 299,407, published Jan. 18, 1989 discloses an extensive series of 4,5-diaryl-1H-pyrazole-1-alkanamides as antiarrhythmic agents.

SUMMARY OF THE INVENTION

In a product aspect the invention relates to compounds of the formula I

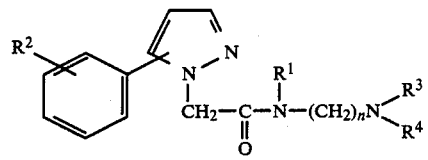

or acid-addition salt thereof wherein $R^1$ is hydrogen or lower-alkyl; $R^2$ is hydrogen, hydroxy, lower-alkyl, lower-alkoxy, lower-alkylamino, lower-alkylamido, lower-alkylsulfonamido, nitro, amino, cyano, or halo; $R^4$ and $R^3$ are independently hydrogen lower-alkyl or hydroxy lower-alkyl or $R^4$ and $R^3$ together form a straight or branched alkylene chain of four to six carbons; and n is an integer from two to eight.

Lower-alkyl as used herein describes linear or branched hydrocarbon chains for four or fewer carbon atoms; lower-alkoxy as used herein describes linear or branched alkyloxy substituents containing four or fewer carbon atoms; halogen describes bromine, chlorine or fluorine.

In a further product aspect, the invention relates to compositions for treating cardiac arrhythmia which comprise compounds of the formula I together with pharmaceutically acceptable excipients or diluents as required.

In a process aspect, the invention relates to a method for treating cardiac arrhythmia in a mammal which comprises administering to said mammal an antiarrhythmically effective amount of a compound of formula I.

A process for preparing a compound of formula I comprises reacting a pyrazole-1-acetate or propanoate with an amine. Further processes for preparing a compound of formula I comprise reacting a 4 to 5-disubstituted pyrazole-1-acetate. or propanoate with an ω-amino linear alkanol, converting the resulting alcohol to a group that is a good substrate for nucleophilic displacement, and displacing said group with an amine.

DETAILED DESCRIPTION INCLUSIVE OF PREFERRED EMBODIMENTS

The synthesis of compounds of the invention may be outlined as shown in scheme A wherein $R^5$ is hydrogen or lower-alkyl.

SCHEME A

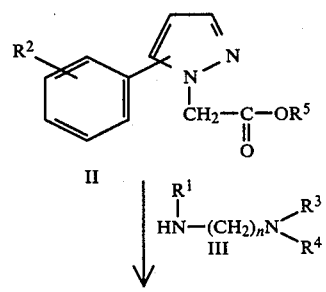

-continued
SCHEME A

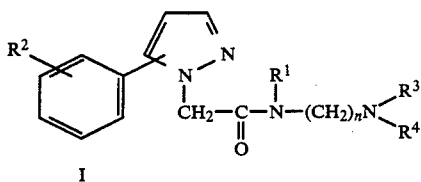

I

A lower-alkyl ester, preferably a methyl or ethyl ester, of a suitably substituted 3-, 4-, or 5-phenylpyrazole-1-alkanoic acid (II) is reacted with an excess of a primary or secondary amine of formula III at 20° to 150° C., preferably at 90° to 150° C. When the amine is valuable, the ester II is preferably reacted with about one equivalent of the amine III in the presence of a tertiary amine, preferably diisopropylethylamine, in an inert solvent.

Alternatively, the compounds of the invention wherein A is $(CH_2)_n$ may be synthesized as outlined in Scheme B:

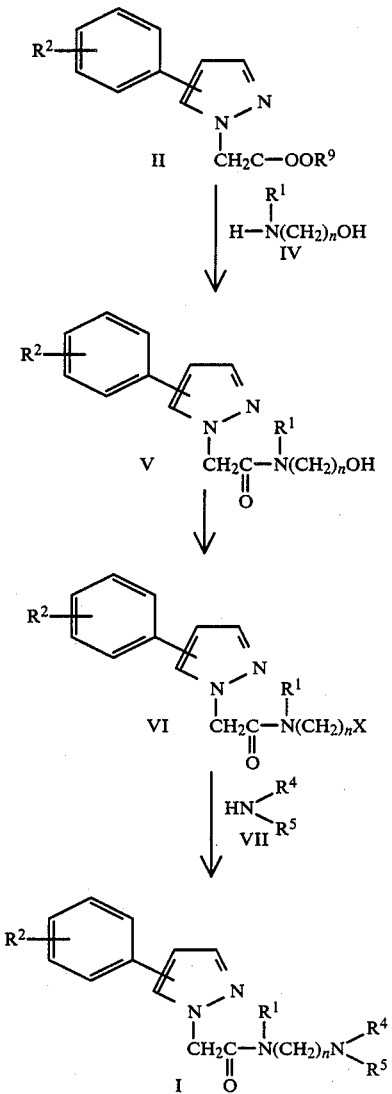

A lower-alkyl ester, preferably a methyl or ethyl ester, of a suitably substituted 3-, 4-, or 5-phenyl-1H-pyrazole-1-alkanoic acid (II) is reacted with an excess of a primary or secondary-aminoalkanol (IV) optionally in the presence of an external base at 20°–150° C., preferably at 90°–100° C. to produce an N-[-hydroxyalkyl]-pyrazole-1-alkanamide of formula V. The hydroxyalkylalkanamide (V) is activated preferably by sulfonylation, preferably with methanesulfonyl chloride, in the presence of a base/solvent such as pyridine at −20° to 20° C., preferably at 0° C., to produce an alkylalkanamide of formula VI wherein X is a group which is subject to nucleophilic displacement such as methanesulfonate.

Alternatively, the hydroxyalkylalkanamide (V) is converted to the corresponding halide (VI, X-Cl, Br or I) by phosphorous trihalide, phosphorus pentahalide, thionyl halide or tetrahalomethane with trialkylphosphine. The group X is then displaced by reaction in the presence or absence of solvent with an appropriate primary or secondary amine (VII) at 20° to 100° C.

The ester II may be synthesized from the appropriately substituted pyrazole by alkylation of the sodium salt with an α-haloacetate or β-halopropanoate, preferably ethyl bromoacetate or ethyl 3-bromopropionate in an inert solvent, preferably DMF, at 20° to 100° C.

The appropriately substituted 3-phenyl-1H-pyrazoles are well known in the literature. The 4-phenyl-1H-pyrazoles may be made by condensation of hydrazine hydrate in an inert solvent, preferably ethanol, at 0°–100°, preferably about 25° C., with the appropriately substituted 2-aryl-3-(dimethylamino-acrolein. The acroleins are avalable from the procedure of Coppola et al. [*J. Het. Chem.* 11, 51–56 (1974)].

The 3-or 5-aryl isomers of ester II may alternatively be synthesized from the appropriately substituted β-ketoenol ether

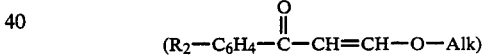

and a hydrazinoacetic acid ester.

The compounds of formula I are useful both in the free base form and the form of acid-addition salts, and both forms are within the purview of the invention. The acid-addition salts are in some cases a more convenient form for use, and in practice the use of the salt form inherently amounts to the use of the base form. The acids which can be used to prepare the acid-addition salts include preferably those which produce, when combined with the free base, medicinally acceptable salts that is, salts whose anions are relatively innocuous to the animal organism in medicinal doses of the salts so that the beneficial properties inherent in the free base are not vitiated by side effects ascribable to the anions. In practicing the present invention it is convenient to form the hydrochloride, fumarate, toluenesulfonate, methanesulfonate, or maleate salts. However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salts is formed only for purposes of purification or identification, or when it is used as an intermediate in preparing a medicinally acceptable salt by ion exchange procedures.

The structures of the compounds of the invention were established by the mode of synthesis, by elemental analysis, and by infrared, ultraviolet, nuclear magnetic resonance, and mass spectroscopy. The course of the reactions and the identity and homogeneity of the products were assessed by thin layer chromatography (TLC) or gas-liquid chromatography (GLC). The starting materials are either commercially available or may be prepared by procedures well known in the art.

In the following procedures melting points are given in degrees C and are uncorrected. The abbreviation THF stands for tetrahydrofuran, DMF stands for N,N-dimethylformamide and Ac stands for the acetyl residue, $CH_3CO$.

EXAMPLE 1

4-Phenyl-1H-Pyrazole

Vilsmeier reagent was prepared by adding 84 mL (0.9 mol) of phosphous oxychloride to 81g (1.1 mol) of DMF with cooling. The reagent was stirred 5 min. and 40.8 g (0.3 mol) of phenylacetic acid in 150 mL of DMF was added dropwise. The mixture was heated at 70° C. for 18 hr, poured onto ice, made basic with 35% aqueous NaOH, filtered free of a solid by-product, and extracted into methylene chloride. The methylene chloride solution was dried over magnesium sulfate and stripped. The residue of 2-phenyl-3-(dimethylamino)acrolein was dissolved in about 350 mL of ethanol and 0.75 mol of hydrazine hydrate was added. The mixture was stirred at room temperature 18 hr and the solid product was filtered off. It was recrystallized from ethanol to yield 35g of 4-phenyl-1H-pyrazole.

By a substantially similar process it is comtemplated that 4-(4-chlorophenyl)-1H-pyrazole, 4-(4-methoxyphenyl)-1H-pyrazole, 4-(3-methylphenyl)-1H-pyrazole, and 4-(2-nitrophenyl)-1H-pyrazole may be made from the corresponding acroleins and hydrazine.

EXAMPLE 2

Ethyl 3-Phenyl-1H-Pyrazole-1-Acetate and Ethyl 5-Phenyl-1H-PYRAZOLEACETATE

A. To a slurry of 8g (0.2 mol) of sodium hydride in 100 mL of DMF at room temperature was added 23g (0.16 mol) of 3-phenylpyrazole. The mixture was stirred 1 hr and 17.8 mL (0.16 mol) of ethyl bromoacetate was added. The reaction was heated at about 100° C. for 2 hr, cooled, poured into water, extracted into methylene chloride, dried over magnesium sulfate and stripped. The resulting oil was chromatographed on silica gel HPLC using 25% ethyl acetate in hexane. The first, and major, component to elute was the 3-isomer. It was recrystallized from ether-hexane to yield 6.0g of ethyl 3-phenyl-1H-pyrazole-1-acetate having an $R_f$ of 0.66 on silica gel in 1:1 ethylacetate-hexane. The third component to elute from the HPLC separation was a minor fraction containing the 5-isomer. Upon stripping the solvent one obtained 1.0g of ethyl 5-phenyl-1H-pyrazole-1-acetate as an oil having an $R_f$ of 0.51 on silica gel in 1:1 ethyl acetate-hexane.

Alternatively 1.18g (0.01 mol) of ethyl hydrazinoacetate hydrochloride and 1.76g (0.01 mol) of 3-ethoxy-1-phenyl-2-propene-1-one were combined with excess of triethylamine and the reaction was heated 20 min. at 100° C. The reaction was cooled, poured into water and extracted into ether. TLC of the ether solution on silica gel with 1:1 ethyl acetate-hexane showed similar distribution of ethyl 3-phenyl-1H-pyrazole-1-acetate and ethyl 5-phenyl-1H-pyrazole-1-acetate to that found in example 2A.

EXAMPLE 3

Ethyl 4-Phenyl-1H-Pyrazole-1-Acetate

To a slurry of 3.0g (0.075 mol) of sodium hydride in 30 mL of DMF at room temperature was added 10g (0.069 mol) of 4-phenyl-1H-pyrazole of example 1. The mixture was stirred 1 hr and 7.8 mL (0.07 mol) of ethyl bromoacetate was added with cooling. The reaction was stirred 3 hr at room temperature, briefly at 100° C. and was poured onto ice. The product was filtered off, rinsed with water, dried, and washed with hexane to yield 14.0g of ethyl 4-phenyl-1H-pyrazole-1-acetate.

EXAMPLE 4

N-[3-(Diethylamino)Propyl]-4-Phenyl-1H-Pyrazole-1-Acetamide

A solution of 13.5g (0.059 mol) of ethyl 4-phenyl-1H-pyrazole-1-acetate of example 3 and 12.6 mL (0.08 mol) of 3-(diethylamino)propanamine in 130 mL of DMF was stirred at 100° C. for 4hr. The reaction was poured into water, extracted into methlene chloride, and stripped. The residue was triturated in ether and the resulting solid was recrystallized from ether-hexane to yield 3.70g of product, mp 55°–57° C.

EXAMPLE 5

N-[3-(Diethylamino)Propyl]-5-Phenyl-1H-Pyrazole-1-Acetamide Hydrochloride

By procedure analogous to that of example 4, but omitting the DMF solvent, the free base of N-[3-(diethylamino)propyl]-5-phenyl-1H-pyrazole-1-acetamide hydrochloride was prepared from 1.0g 4.3 mmol) of ethyl 5-phenyl-1H-pyrazole-1-acetate and 3-(diethylamino)propanamine. The hydrochloride salt was prepared by dissolving the free base (an oil) in ethanol, adding a solution of hydrogen chloride in anhydrous ether, and recrystallizing the resulting solid from ethanol-ether. Upon drying, the white, crystalline product collapsed to a brownish, amorphous solid.

EXAMPLE 6

3-(3-Chlorophenyl)-N-[6-Dimethylamino)Hexyl]-1H-Pyrazole-1-Acetamide

By a procedure substantially similar to that of example 4, it is contemplated that 3-(3-chlorophenyl)-N-[6-(dimethylamino)hexyl]-1H-pyrazole-1-acetamide may be synthesized from ethyl 3-(3-chlorophenyl)-1H-pyrazole-1-acetate and 6-(dimethylamino)hexanamine.

EXAMPLE 7

4-(4-Methoxyphenyl)-N-[2-(Piperidinyl)Ethyl]-1H-Pyrazole-1-Acetamide

By a procedure substantially similar to that of example 4, it is contemplated that 4-(4-methoxyphenyl)-N-[2-(1-piperidinyl)ethyl]-1H-pyrazole-1-acetamide may be synthesized from ethyl 4-(4-methoxyphenyl)-1H-pyrazole-1-acetate and 1-(2-aminoethyl)piperidine.

EXAMPLE 8

N-[3-(Diethylamino)Propyl]-5-(3-Nitrophenyl)-1H-Pyrazole-1-Acetamide

By a procedure substantially similar to that of example 4, it is contemplated that N-[3-(diethylamino)propyl]-5-(3-nitrophenyl)-1H-pyrazole-1-acetamide may be synthesized from ethyl 5-(3-nitrophenyl)-1H-pyrazole-1-acetate and 3-(diethylamino)-N-methylpropanamine(N,N-diethyl-N-methylpropylenediamine).

Other embodiments of the invention may be synthesized from the appropriate phenylpyrazoles by additional methods which are disclosed in U.S. application D.N. 7398C of Denis M. Bailey which is incorporated herein by reference.

The antiarrhythmic activity of compounds of the invention was demonstrated by the following procedure.

Duncan Hartley guinea pigs (600–900 grams) either sex were anesthetized with urethane (1.4g/kg, i.p.) and supplemented as needed. An intravenous route for drug administration was established using microbore tubing inserted into the jugular vein. The induction of arrhythmias by aconitine hydrochloride (34 g/kg) was evaluated in control guinea pigs given 1 cc saline as an intravenous bolus 10 minutes prior to aconitine challenge.

Compounds to be tested were administered intravenously 10 minutes prior to aconitine challenge at an initial dosage of 30 mg/kg. This dosage was reduced in subsequent animals if severe cardiac rhythm disturbances persisted beyond two minutes after injection in the first guinea pig tested. All drugs were tested at the maximally tolerated dose (identified by the lack of arrhythmias in the EKG prior to aconitine challenge). Compounds were administered in saline as 1 cc bolus injections (n=5–9).

Time intervals between aconitine injection and the appearance of arrhythmias were determined. Specifically noted was the time until the onset of (i) the first premature ventricular contraction (PVC); (ii) the first sustained run of ventricular tachycardia consisting of 10 or more ventricular beats (VTACH); and (iii) the time until the appearance of ventricular fibrillation lasting longer than 15 seconds (VFIB). The average time and standard error of the mean until the appearance of these arrhythmias were calculated for each treatment group and compared to concurrent controls using a one-way analysis of variance. Activity was defined as a statistically significant delay in the onset of PVC, VTACH and VFIB time course compared to control values.

The following table summarizes the results obtained from the testing of representative compounds of the invention.

| Example No. | Minutes to | | |
|---|---|---|---|
| | PVC | VTACH | VFIB |
| Control | 1.8–1.9 | 2.4–2.5 | 4.2–7.0 |
| 4 | 8.0 | 13.4 | 43.2 |
| 5 | 6.0 | 8.3* | 14.8 |

*not statistically significant

The compounds of the invention can be prepared for use by conventional pharmaceutical procedures; that is, by dissolving or suspending them or their pharmaceutically acceptable salts in a pharmaceutically acceptable vehicle, e.g., water, aqueous alcohol, glycol, oil solution or oil-water emulsion, for parenteral or oral administration; or by incorporating them in unit dosage form as capsules or tablets for oral administration either alone or in combination with conventional adjuvants or excipients, e.g., calcium carbonate, starch, lactose, talc, magnesium stearate, gum acacia, and the like.

The percentage of active component in the composition and method for treating or preventing arrhythmia can be varied so that a suitable dosage is obtained. The dosage administered to a particular patient is variable depending upon the clinician's judgement using as the criteria: the route of administration the duration of treatment, the size and condition of the patient, the potency of the active component, and the patient's response thereto. An effective dosage amount of active component can thus be determined by the clinician considering all criteria and utilizing his best judgement on the patient's behalf.

I claim:

1. A compound of formula:

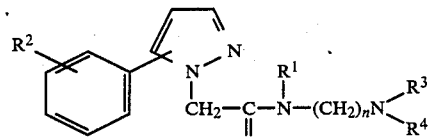

or acid-addition salt thereof wherein $R^1$ is hydrogen or lower-alkyl; $R^2$ is hydrogen, hydroxy, lower-alkyl, lower-alkoxy, lower-alkylamino, lower-alkylamido, lower-alkylsufonamido, nitro, amino, cyano, or halo; $R^3$ and $R^4$ are independently hydrogen lower-alkyl or hydroxy lower-alkyl, or $R^4$ and $R^3$ together form a straight or branched alkylene chain of four to six carbons; and n is an integer from two to eight.

2. A compound according to claim 1 wherein $R^1$ is hydrogen.

3. A compound according to claim 2 wherein n is two or three.

4. A compound according to claim 3 wherein $R^3$ and $R^4$ are ethyl.

5. N-[3-(Diethylamino)propyl]-4]phenyl-1H-pyrazole-1-acetamide according to claim 4.

6. A composition for treating cardiac arrhythmias comprising an amount of a compound according to claim 1 effective to treat cardiac arrhythmias together with one or more pharmaceutically acceptable excipients or diluents.

7. A composition for treating cardiac arrhythmias comprising an amount of a compound according to claim 4 effective to treat cardiac arrhythmias together with one or more pharmaceutically acceptable excipients or diluents.

8. A composition for treating cardiac arrhythmias comprising an amount of N-[3-(diethylamino)propyl]-4-phenyl-1H-pyrazole-1-acetamide or pharmaceutically acceptable acid addition salt thereof according to claim 5 effective to treat cardiac arrhythmias together with one or more pharmaceutically acceptable excipients or diluents.

9. A method for treating cardiac arrhythmias in a susceptible subject which comprises the step of administering an amount of a compound according to claim 1 effective to treat cardiac arrhythmias.

10. A method for treating cardiac arrhythmias in a susceptible subject which comprises the step of administering an amount of a compound acording to claim 4 effective to treat cardiac arrhythmias.

11. A method for treating cardiac arrhythmias in a susceptible subject which comprises the step of administering an amount of N-[3-(diethylamino)propyl]-4-phenyl-1H-pyrazole-1-acetamide or pharmaceutically acceptable acid addition salt thereof according to claim 5 effective to treat arrhythmias.

* * * * *

UNITED STATES PATENT AND TRADEMARK OFFICE
CERTIFICATE OF CORRECTION

PATENT NO. : 4,888,352

DATED : December 19, 1989

INVENTOR(S) : Denis Mahlon Bailey and Virendra Kumar

It is certified that error appears in the above-identified patent and that said Letters Patent is hereby corrected as shown below:

Column 1, line 31: "2[(5-phenyl" should read --- 2-[(5-phenyl ---.

Column 1, line 36: "β-[1(3" should read --- β-[1-(3 ---.

Column 1, line 41: "Nalkyl" should read --- N-alkyl ---.

Column 1, line 57: "dimethyl3" should read --- dimethyl-3 ---.

Column 1, line 59: "trimethyl3" should read --- trimethyl-3 ---.

Column 1, line 65: "diphenyl1H" should read --- diphenyl-1H ---.

Column 2, line 43: "4 to 5" should read --- 4 or 5 ---.

Column 4, line 11: "alkyalkanamide" should read --- alkylalkanamide ---.

Column 4, line 16: "X-Cl" should read --- X=Cl ---.

Column 4, line 32: "(dimethylamino-acrolein" should read --- (dimethylamino)acrolein ---.

Column 5, line 52: "PYRAZOLEACETATE" should read --- Pyrazoleacetate ---.

Column 6, line 3: " Alternatively" should read --- B. Alternatively ---.

Column 7, line 21: "(N,N-diethyl-N-methyl" should read --- (N,N-diethyl-N'-methyl ---.

UNITED STATES PATENT AND TRADEMARK OFFICE
CERTIFICATE OF CORRECTION

PATENT NO. : 4,888,352

DATED : December 19, 1989

INVENTOR(S) : Denis Mahlon Bailey and Virendra Kumar

It is certified that error appears in the above-identified patent and that said Letters Patent is hereby corrected as shown below:

Column 7, lines 32 & 33 "grams) either sex" should read --- grams) of either sex ---.

Column 8, line 26: "route of administration the" should read --- route of administration, the ---.

Column 8, line 57 (Claim 5): "propyl]-4]phenyl" should read --- propyl]-4-phenyl ---.

Column 3, line 57 (Scheme B in the structure for VII: "$R^5$" should read --- $R^3$ ---.

Column 3, line 66 (Scheme B in the structure for I: "$R^5$" should read --- $R^3$ ---.

Column 4, line 6: "N-[ -hydroxyalkyl]" should read --- N-[$\omega$-hydroxyalkyl] ---.

Claim 1, line 47: "hydrogen lower-alkyl" should read --- hydrogen, lower-alkyl ---.

Signed and Sealed this

Thirteenth Day of August, 1991

Attest:

HARRY F. MANBECK, JR.

Attesting Officer

Commissioner of Patents and Trademarks